United States Patent [19]

Takamura et al.

[11] Patent Number: 4,697,894
[45] Date of Patent: Oct. 6, 1987

[54] CONNECTION DEVICE FOR CONNECTING AN ASSOCIATED UNIT TO AN EYEPIECE SECTION OF AN ENDOSCOPE

[75] Inventors: Koji Takamura; Takamasa Hosoya; Kazunari Kobayashi, all of Tokyo, Japan

[73] Assignee: Olympus Optical Co., Ltd., Tokyo, Japan

[21] Appl. No.: 802,250

[22] Filed: Nov. 27, 1985

[30] Foreign Application Priority Data

Nov. 30, 1984 [JP] Japan .................................. 59-233078
Nov. 30, 1984 [JP] Japan .................................. 59-182018

[51] Int. Cl.⁴ .............................................. G02B 7/00
[52] U.S. Cl. .................................................. 350/574
[58] Field of Search ............... 350/252, 257, 255, 321, 350/319, 502, 574; 285/276, 277, 305, 388

[56] References Cited

U.S. PATENT DOCUMENTS 3,640,424 2/1972 Ando ..................................... 350/589
3,740,114 6/1973 Thompson ............................ 350/589

FOREIGN PATENT DOCUMENTS

6926837 6/1969 Fed. Rep. of Germany .
2723652 12/1977 Fed. Rep. of Germany .
58-166302 11/1983 Japan .
2053506 2/1981 United Kingdom .

Primary Examiner—John K. Corbin
Assistant Examiner—Vincent J. Lemmo

[57] ABSTRACT

A connecting device includes a first connecting section to which a camera is detachably connected, and a second connecting section detachably connected to an eyepiece section of an endoscope. The first connecting section has a main body which includes a circular fitting recess with an inner surface and support holes each of which opens into the inner surface and extends radially. Locking bodies are disposed in the respective holes. Each locking body has a slidable portion movable in the corresponding hole along the axial direction thereof, and a semispherical pressing portion. A clamp ring is rotatably provided on the main body. When the clamp ring is rotated, the locking bodies are pressed into the recess so that the pressing portions abut against the outer surface of the eyepiece section fitted in the recess.

11 Claims, 12 Drawing Figures

CONNECTION DEVICE FOR CONNECTING AN ASSOCIATED UNIT TO AN EYEPIECE SECTION OF AN ENDOSCOPE

BACKGROUND OF THE INVENTION

This invention relates to a connection device for detachably connecting an associated unit such as a camera to an eyepiece section of an endoscope.

Recently, a method has been adopted which allows observation of body cavities through, for example, a camera connected to an eyepiece section of an endoscope. Usually the camera is connected to the eyepiece section through a connection device. British Patent No. 2,053,506 and West German Utility Model No. 6,926,837 disclose this type of known connection device. This connection device has an annular member to which the eyepiece section of an endoscope is connected and in which a plurality of balls are arranged along its inner surface. The balls are depressed by a locking ring on the outer periphery of the annular member, causing them to be projected into the annular member. As a result, the balls are brought into engagement with the eyepiece section, whereby the eyepiece section is locked onto the annular member.

The balls are disposed in holes formed in the wall of the annular member. In order to retain the balls in the holes, each hole has a diameter smaller than that of the balls. For this reason, the balls can be projected through the holes into the annular member only to an extent corresponding to less than one half the size of the balls, the diameter of the balls in relation to the diameter of the holes being the limiting factor. Thus, the connection device finds restricted application with particular endoscopes. It cannot be applied to an endoscope of a type whose eyepiece section differs somewhat in diameter or in the inclination of its taper section, yet many kinds of endoscopes are known whose eyepiece sections differ in size. For obvious reasons it is not economical to have to use a different connection device on each and every occassion according to the particular size of a given eyepiece section of an endoscope.

SUMMARY OF THE INVENTION

It is accordingly the object of this invention to provide a connection device adaptable for application to a wide variety of endoscopes regardless of the size of their eyepiece sections.

In order to achieve the above-mentioned object there is provided a connection device comprising a first connecting section to which an associated unit is detachably connected, and a second connecting section detachably connected to an eyepiece section of an endoscope, the second connecting section comprising a main body having a circular fitting recess to which the eyepiece section is fitted, a plurality of support holes each opened at the inner surface of the recess and extending in the radial direction of the recess, a plurality of locking bodies movable in the respective support holes to extend into the recess to hold the eyepiece section in the recess, each locking body having a slide portion arranged in the support hole to be movable along the axial direction of the support hole, and a pressing portion extending from one end of the slide portion through the support hole into the recess to abut against the outer surface of the eyepiece section; means for preventing the slide portion from slipping out of the support hole, and a clamp member supported on the main body external of the locking bodies and movable between a press position where it pushes the locking bodies toward the recess and an open position wherein the locking bodies are released from their pushed state.

BRIEF DESCRIPTION OF THE DRAWINGS

FIGS. 2 to 8 show a connection device according to one embodiment of this invention, in which

DETAILED DESCRIPTION OF THE PREFERRED EMBODIMENT

A connection device according to one embodiment of this invention will be explained with reference to the accompanying drawings.

Figure 1:
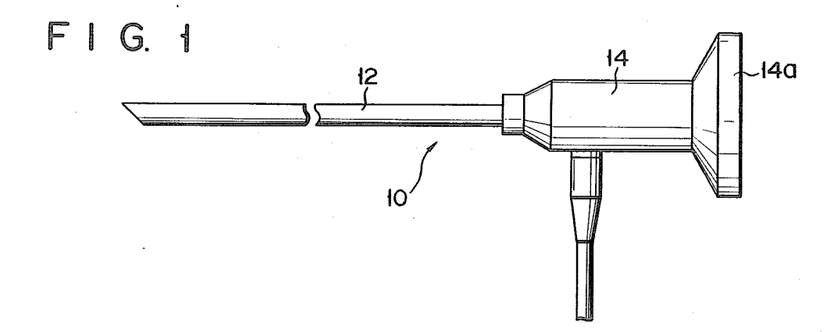
FIG. 1 is a side view showing a hardscope.

FIG. 1 shows an endoscope, for example, a hardscope 10. The endoscope 10 includes an optical viewing tube 12 adapted for insertion into a body cavity, and an eyepiece section 14 mounted on the end of the optical viewing tube 12. A proximal end 14a of the eyepiece section 14 is so formed as to have a truncated cone shape. The taper angle of the basic end 14a differs from hardscope to hardscope.

Figure 2:
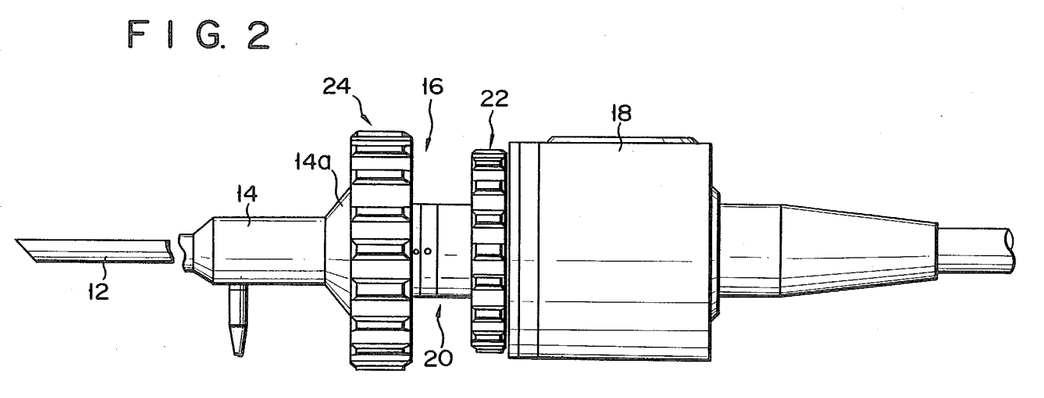
FIG. 2 is a side view of the device through which a TV camera is connected to an eyepiece of a hardscope.
Figure 3:
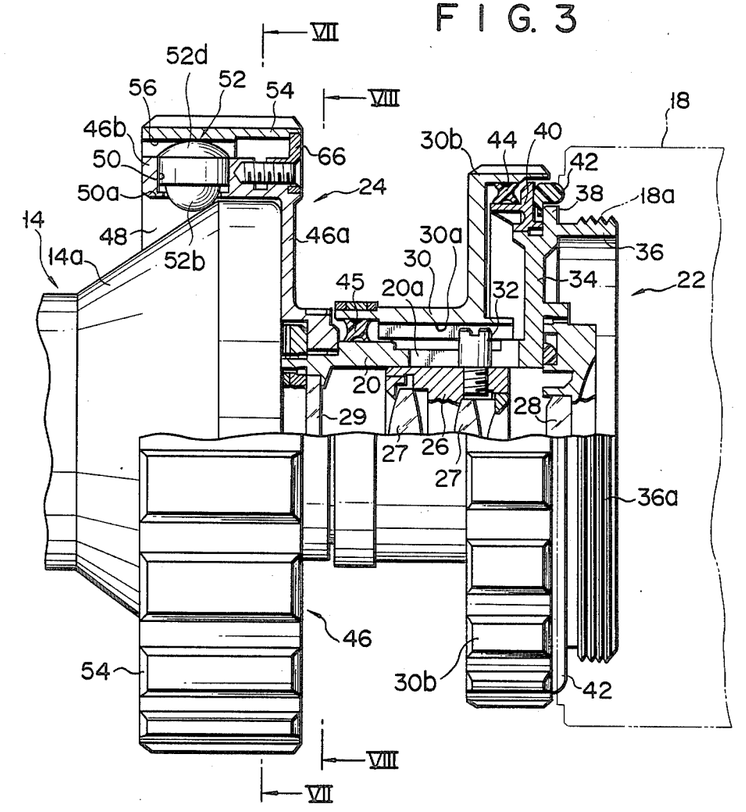
FIG. 3 is a partially broken side view of the device.

FIG. 2 shows a state wherein an image pickup device 18 such as a TV camera is connected through a connection device 16 to the proximal end 14a of a hardscope. As shown in FIGS. 2 and 3, the connection device 16 includes a lens barrel 20, a first connecting section 22 provided at one end of the lens barrel and connected to the image pickup device 18, and a second connecting section 24 provided at the other end of the lens barrel and connected to the eyepiece section 14 of the hardscope 10. Within the lens barrel 20 is disposed an annular lens frame 26 which is movable along the axial direction of the lens barrel. A plurality of lenses 27 are fitted in the lens frame 26. Windows 28 and 29 made of a sheet glass are blocked one at each end of the lens barrel 20 to hermitically seal the interior of the lens barrel.

A focus adjustment ring 30 is rotatably fitted over the entire periphery of the lens barrel 20. The rotation of the adjustment ring 30 permits the lens frame 26 to be moved in the axial direction of the lens barrel 20, i.e., along the optical axis of the lenses 27. Stated in more detail, an axially extending, elongated groove 30a is formed on the inner surface of the adjustment ring 30 and a spiral guide through-hole 20a is so formed in the lens barrel 20 as to correspond to the elongated groove 30a. A guide pin 32 is fastened to the outer periphery of the lens barrel 20 and extends through the guide hole 20a into the elongated groove 30a of the adjustment ring 30. The rctation of the adjustment ring 30 causes the guide pin 32 to be pressed by the side edge of the elongated groove 30a to permit the guide pin 32 to be moved along the guide hole 20a. As a result, the lens 27 is moved, together with the lens frame 26, to permit an adjustment in focal position to be made. One end portion of the adjustment ring 30 extends outward radially to provide a gripping portion 30b by which to rotate the adjustment ring.

A flange 34 extends outward radially from one end of the lens barrel 20 and a mounting cylinder 36 extends from the outer periphery of the flange, coaxially with the lens barrel. An external threaded portion 36a is provided on the outer periphery of the mounting cylinder 36 and engages with an internal threaded portion 18a of an image pickup device 18 as the associated unit to be connected. That is, the flange 34 and mounting cylinder 36 provide the first connecting section 22 to which such an associated unit is to be connected. An annular projection 38 is formed on the outer periphery of the mounting cylinder 36 so that it abuts against the front end of the image pickup device 18 when the external threaded portion 36a of the mounting cylinder 36 is brought into threaded engagement with the image pickup device. An annular fixing frame 40 is mounted on the outer periphery of the flange 34 such that it is located opposite the annular projection 38. An annular sealing member 42 is placed between the fixing frame 40 and annular projection 38 and adapted, when the image pickup device 18 is connected to the first connecting section 22, to be brought into liquid-tight contact with the front end of the image pickup device.

Figure 4:
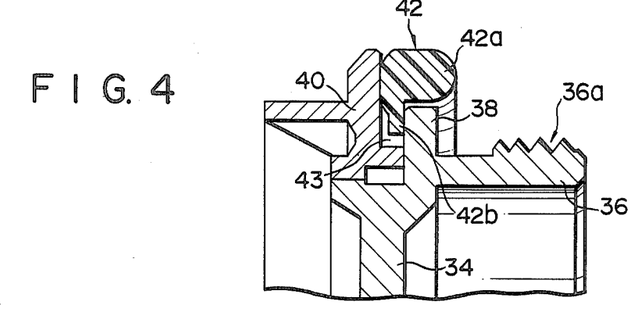
FIG. 4 is an enlarged sectional view showing a part of the connection device.

As shown in FIG. 4, the sealing member 42 is made of an elastic member and comprised of a body 42a with an elliptical cross-section and a fixing portion 42b radially extending inward from the body. The fixing portion 42b is fitted into a recess 43 defined between the projection 38 and the fixing frame 40. By doing so, the body 42a of the sealing member 42 extends over the projection 38 toward the image pickup device 18.

As shown in FIG. 3, a ring-like packing 44 is placed between the inner surface of the gripping portion 30b of the adjustment ring 30 and the fixing frame 40, and a ring-like packing 45 is placed between the inner peripheral surface of the other end portion of the adjustment ring and the lens barrel 20. These packings 44 and 45 are made of an elastic material having a substantially crisscross section. Since the packing has such a cross-section, it encounters less frictional resistance, making it possible both to reduce the rotating force required to rotate the adjustment ring 30 and to improve operablity.

Figure 5:
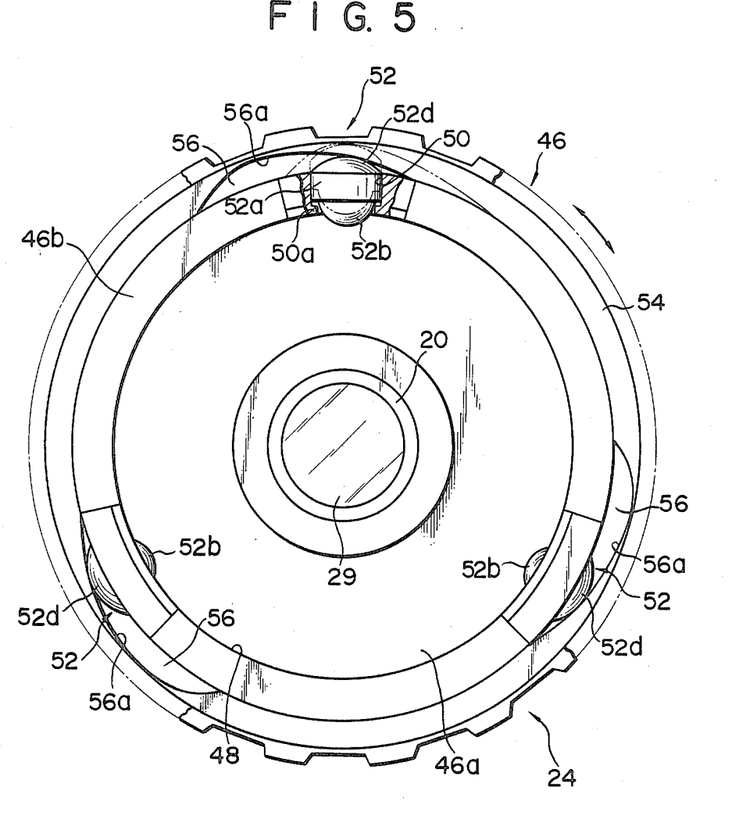
FIG. 5 is a front view of the connection device.

As shown in FIGS. 3 and 5, the second connecting section 24 connected to the eyepiece section 14 of the hardscope 10 includes a main body 46 having a flange 46a externally extending from the outer periphery of the other end portion of the lens barrel 20, and a connection cylinder 46b extending from the external edge of the flange, coaxially with the lens barrel. A mounting recess 48 is defined by the inner wall of the flange 46a and inner wall of the connection cylinder 46b and receives the base end portion 14a of the eyepiece section 14. The diameter of the recess 48, that is, the inner diameter of the connection cylinder 46b is slightly greater than that of the base end portion 14a of the eyepiece section.

Figure 6:
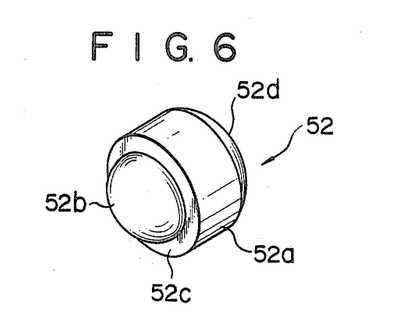
FIG. 6 is a perspective view of a locking body.

Three support holes 50 are formed in the connection cylinder 46b such that they are equidistantly arranged along the circumference of the connection cylinder and extend radially. An inwardly extending, annular stopper 50a is formed on the edge of that end of the respective support hole which opens into the inner surface of the connection cylinder 46b. Locking bodies 52, for holding the base end portion 14a of the eyepiece section fitted in the recess 48, is movably inserted into the respective support holes 50. As shown in FIGS. 3, 5 and 6, each locking body 52 has a cylindrical slide portion 52a, axially slidable in the support hole 50 and having a diameter slightly smaller than that of the support hole, and a semispherical pressing portion 52b projecting from one end of the slide portion. The pressing portion 52b has a diameter smaller than the diameter of the slide portion 52a and inner diameter of the stopper 50a, and an annular shoulder 52c is formed between the slide portion and the pressing portion. The slide portion 52a is movable in the direction of the recess 48 to a position where the shoulder 52c abuts against the stopper 50a. When the slide portion 52a moves toward the recess 48 the pressing portion 52b projects into the recess through the open end of the support hole 50. The other end 52d of the slide portion 52a is formed in a spherical shape having a relatively large diameter.

A clamp cylinder 54, for pushing the locking bodies 52 toward the recess 48, is rotatably fitted over the outer periphery of the connection cylinder 46b. Three recesses 56 are formed in the inner surface of the clamp cylinder 54 to correspond to the three locking bodies 52. As better seen from FIG. 5, each recess 56 extends along the circumference of the clamp cylinder 54 such that it is gradually deepened in a clockwise direction. The bottom surface of each recess 56 forms a cam surface 56a which presses the end 52d of the corresponding locking body 52. The rotation of the clamping cylinder 54 causes the end 52d of each locking body 52 to be pressed by the corresponding cam surface 56a, with the result that the pressing portion 52b of each locking body is projected into the recess 48. As indicated by dash and dot lines in FIG. 5, in the open position where the deepest portion of each recess 56 confronts the locking body 52, the locking bodies are not pressed by the cam surface 56a. In the open position, the respective locking body 52 is movable to a position where the pressing portion 52b is held in the support hole 50, that is, in a retracted position. When the clamp cylinder 54 is rotated counterclockwise from the open position, each locking body 52 is pressed by the corresponding cam surface 56a to project into the recess 48. The extent of the projection of the pressing portion 52b of the locking body 52 becomes greater as the clamp cylinder 54 is rotated in the counterclockwise direction. The clamp cylinder 54 can be rotated to a maximum press position wherein the shoulder 52c of the locking body 52 abuts against the stopper 50. In this connection it is to be noted that the extent of the projection of the pressing portion 52b becomes maximal in the maximum press position.

Figure 7:
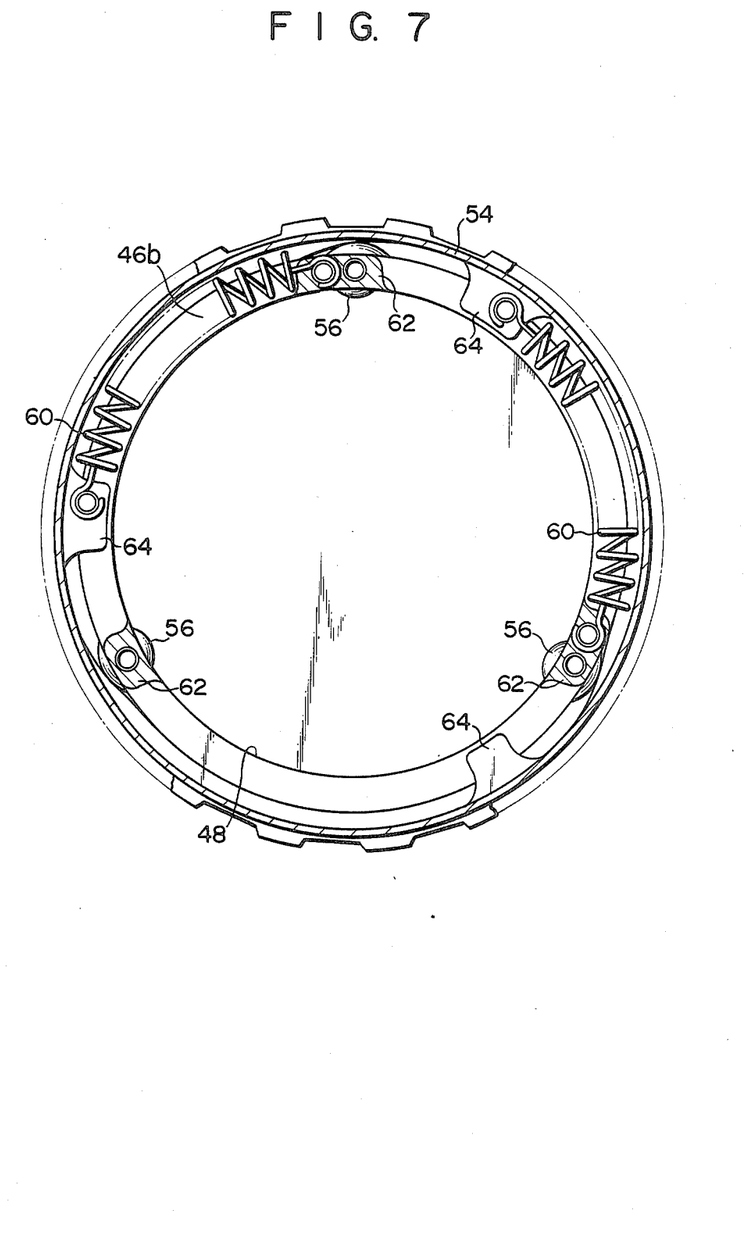
FIG. 7 is a sectional view taken along line VII—VII of FIG. 3.

As shown in FIG. 7, a pair of tension springs 60 are stretch between the connection cylinder 46b and clamp cylinder 54 to urge the clamp cylinder in the clockwise direction, i.e., in the maximum press position. For this reason, the clamp cylinder 54 is usually located at the maximum press position and thus the locking bodies 52 are urged into the recess 48. The springs 60 are stetched along the circumference of the connection cylinder 46b and clamp cylinder 54. Each spring 60 is connected at one end to a projection 62 on the connection cylinder 46b and at the other end to a projection 64 on the clamp cylinder 54.

Figure 8:
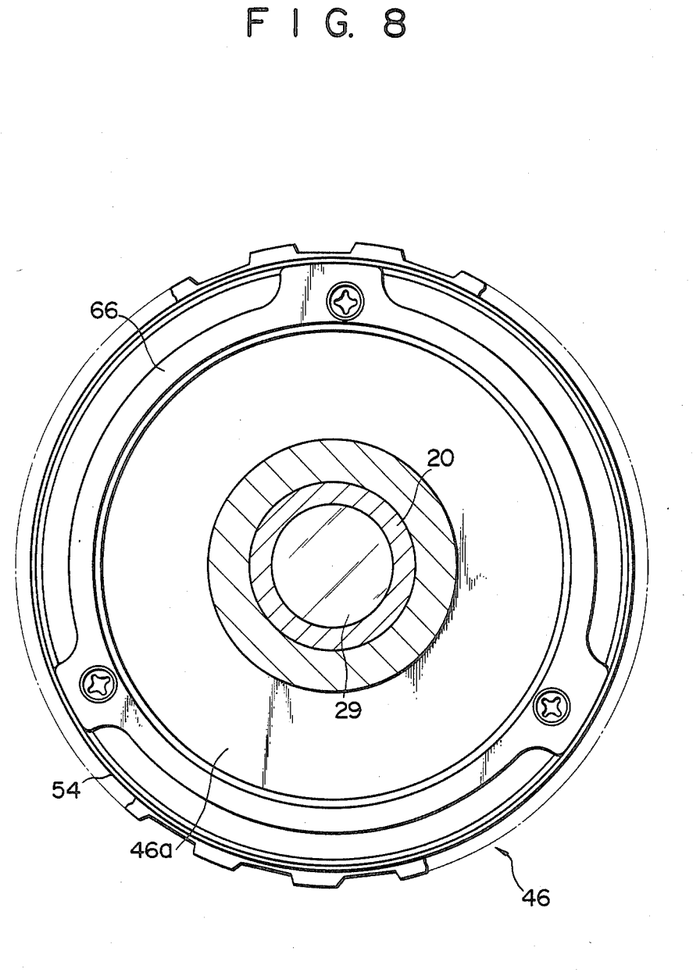
FIG. 8 is a sectional view taken along line VIII—VIII of FIG. 3.

As shown in FIG. 8, an annular back plate 66 is threaded onto the projections 62 of the connection cylinder 46b. The back plate 66 prevents the clamp cylinder 54 from slipping off the connection cylinder 46b and at the same time serves as a decorative panel.

The operation of applying the connection device having the above construction is as follows. First, the external threaded portion 36a of the first connecting section 22 is brought into threaded engagement with the internal threaded portion 18a of the image pickup device 18, thus connecting the image pickup device to the connection device. In this case, the sealing member 42 abuts against the front end of the image pickup device 18, thereby providing a liquid-tight seal between the connection device and the image pickup device.

Then, the base end portion 14a of the eyepiece section 14a of the hardscope 10 is inserted within the recess 48 of the second connecting section 24. At this time, the clamp cylinder 54 is rotated against the urging force of the tension springs 60 and held in the open position. Even if the locking bodies 52 are projected into the recess 48, the base end portion 14a of the eyepiece section 14 can readily push the locking bodies back into the support holes 50. The base end portion 14a is inserted into the recess 48 with its end surface in abutment with the bottom surface of the recess 48, i.e., the flange 46a, and then a force acting on the clamp cylinder 54 is released. Then, the clamp cylinder 54 is automatically rotated toward the maximum press position by the springs 60. Thus, each cam surface 56a of the clamp cylinder 54 presses the end 52d of the corresponding locking body 52, causing the locking body to be forced toward the recess 48. In consequence, the pressing portions 52b of the locking bodies 52 are projected into the recess 48 and pressed against the tapering surface of the base end portion 14a of the eyepiece section 14. The locking bodies 52 and clamping cylinder 54 are retained, under the urging force of the springs 60, in the state in which the pressing portions 52b of the locking bodies abut against the tapering surface of the base end portion 14a. Thus, the base end portion 14a is held within the recess 48 and, in this way, the connection device is connected to the hardscope 10.

In the state in which the image pickup device 18 is connected through the connection device to the eyepiece section 14 of the hardscope, the eyepiece section is optically connected by the lens barrel 20 to the image pidkup device and an optical image emitted from the eyepiece section is sent to the image pickup device via the lens 27 within the lens barrel.

Where the connection device is removed from the eyepiece section 14 of the hardscope, the clamp cylinder 54 is rotated to the open position against the urging force of the springs 60. Under this condition, if the eyepiece section 14 is withdrawn from the recess 48, the base end portion 14a of the eyepiece section 14 pushes the locking bodies 52 back into the support holes 50.

In the connection device having the above construction, each of the locking bodies includes the slide portion 52a, slidably inserted into the support hole of the connection cylinder 46b, and a pressing portion 52b, projecting from the slide portion, and is so constructed that only the pressing portion is projected into the recess 48. For this reason, the pressing portion 52b is projected to a greater extend than the conventional, balltype locking body. Thus, even if eyepiece sections whose tapered surfaces differ in inclination are mounted in the recess 48, the locking bodies can be brought into positive, abutting engagement with the tapered surface of the eyepiece section. It is, therefore, possible to apply the connection device to various types of endoscopes.

The sealing member 42, abutting against the front surface of the image pickup device when the image pickup device is connected to the connection device, is fixed to the mounting cylinder 36 by fitting the fixing portion 42b into the recess 43 defined between the projection 38 of the mounting cylinder and the fixing frame 40. For this reason, the sealing member 42 can be positively fixed to the mounting cylinder 36, in contrast to the case where an adhesive agent is used. It is, therefore, possible to prevent the sealing member 42 from slipping off the mounting cylinder 36 for a prolonged period of time. As a result, an adequate seal can be assured between the connection device and the image pickup device.

Figures 9, 10:
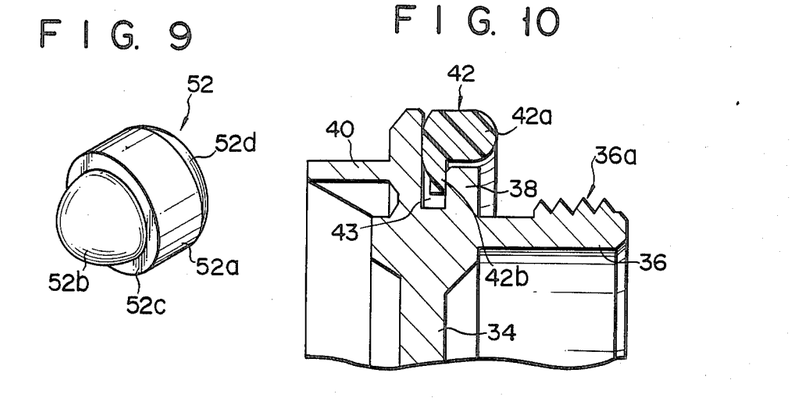
FIG. 9 is a perspective view showing a modified form of a locking body.
FIGS. 10 to 12 are sectional views showing different modifications of a sealing member.

This invention is not restricted to the above-mentioned embodiment. Various changes or modifications can be made without departing from the spirit and scope of this invention. Although in the above-mentioned embodiment the pressing portion of the locking body is of a semispherical configuration, any other suitable configuration may be adopted. As shown in FIG. 9, for example, the pressing portion 52b may be of a semispheroidal configuration, in which case the pressing portion can be projected to a still greater extent.

Figure 11:
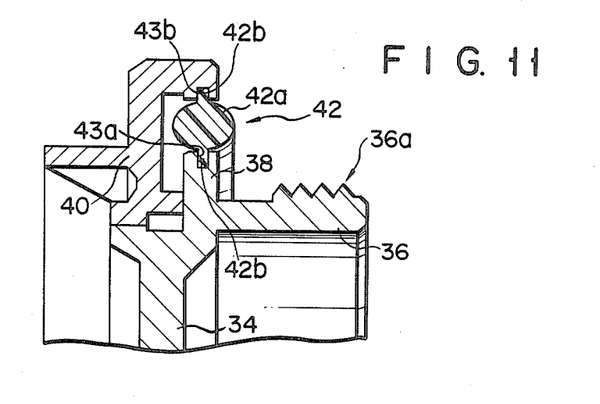
Figure 12:
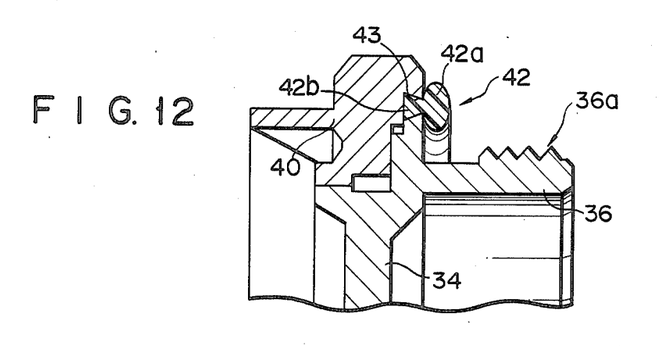

The sealing member 42 may be mounted in the manner shown in FIGS. 10 to 12. In the modification shown in FIG. 10, a fixing frame 40 is formed integral with the flange 34 of the first connecting section and a fixing portion 42b of the sealing member 42 is fitted into a groove 43 formed at the outer periphery of the flange 34. In the modification shown in FIG. 11, the sealing member 42 has a pair of fixing portions 42a and 42b projecting from the body 42a in opposite directions. One of the fixing portions 42a and 42b is fitted into a mounting recess 43a formed at the forward end face of the projection 38 of the mounting cylinder 36 and the other is fitted into a mounting recess 43b of the fixing frame 40 which is formed opposite to the recess 43a. In the modification shown in FIG. 12, a wedge-like recess 43 is provided by the forward end face of a projection 38 and fixing frame 40. The fixing portion 42b of sealing member 42 is accordingly, of a wedge-like configuration complementary to recess 43.

In the first to third modifications, it is possible to affix the sealing member with certainty to the mounting cylinder, as in the first embodiment of this invention.

What is claimed is:

1. A connection device for connecting an associated unit to an eyepiece section of an endoscope, comprising:
   a connecting section detachably connected to the eyepiece section of the endoscope;
   said connecting section including;
   a main body having a fitting recess with a circular inner surface in which said eyepiece section is fitted, and a plurality of support holes each of which opens into the inner surface of the recess and extends in the radial direction of the recess;
   a plurality of locking bodies for holding the eyepiece section fitted to the recess, each of said locking bodies having a cylindrical slide portion which has a diameter slightly smaller than that of the corresponding support hole and is slidable in the corresponding support hole along the axial direction of the support hole, and a pressing portion projected into the recess from that end surface of the slide portion which is located at the recess side, through movement of the slide portion, to abut against an outer surface of said eyepiece section;

means for preventing the slide portions from slipping out of the respective support hole, said means having projections, each extending inward from the open end edge of the corresponding support hole on the recess side and capable of abutting against said end surface of the slide portion; and a clamp member supported on the main body external of the locking bodies and movable between a press position where it pushes the locking bodies into the recess and an open position wherein the locking bodies are released from their pushed state.

2. A connection device according to claim 1, wherein each of said pressing portions is of a semi-spherical configuration having a diameter slightly smaller than that of the slide portion and arranged coaxial therewith.

3. A connection device according to claim 1, wherein each of said pressing portions is of a semi-spheroidal configuration and formed concentric with the slide section.

4. A connection device according to claim 1, wherein said connecting section includes urging means for urging the clamp member toward the press position.

5. A connection device according to claim 1, comprising another connecting section to which the associated unit is detachably connected and which includes a sealing member which, when the another connecting section is connected to the associated unit, abuts against the associated unit in a liquid-tight fashion to permit a seal to be obtained between the associated unit and the connecting device.

6. A connection device according to claim 5, wherein said another connecting section includes a mounting cylinder disposed concentric with the recess, and a threaded portion formed on the outer periphery of the mounting cylinder and adapted to be brought into threaded engagement with the associated unit, and said sealing member is of an annular configuration and is fitted over the outer periphery of the mounting cylinder.

7. A connection device according to claim 6, wherein said mounting cylinder has an annular mounting groove on its outer periphery, and said sealing member has an annular body adapted to engage with the associated unit and a fixing portion projecting from the annular body and fitted into the mounting groove.

8. A connection device according to claim 5, which further comprises: a lens barrel provided, coaxial with the fitting recess, between the two connecting sections, a lens system movable within the lens barrel along the axis of the lens barrel, and adjusting means for moving the lens system to adjust its focal position.

9. A connection device for connecting an image pickup device to an eyepiece section of an endoscope, comprising:

a first connecting section to which the image pickup device is detachably connected;

a second connecting section detachably connected to the eyepiece section of the endoscope; and a lens barrel, provided between the first and second connecting sections, for optically connecting the image pickup device connected to the connecting section to the eyepiece section connected to the second connecting section;

said second connecting section including:

a main body including a fitting recess with a circular inner surface in which the eyepiece section is fitted, and a plurality of support holes each of which opens into the inner surface of the recess and extends in a radial direction of the recess;

a plurality of locking bodies for holding the eyepiece section fitted in the recess, each of said locking bodies having a slide portion slidable in the corresponding support hole along the axial direction thereof and a pressing portion projected into the recess, through movement of the slide portion, to abut against the outer surface of said eyepiece section;

means for preventing the slide portions from slipping out of the respective support holes; and a clamp member supported on the main body external of the locking bodies and movable between a press position where it pushes the locking bodies into the recess and an open position wherein the locking bodies are released from their pushed state.

10. A connection device according to claim 9, wherein said lens barrel includes a lens system movable within the lens barrel along the axis of the lens barrel, and adjusting means for adjusting the focal position of the lens system.

11. A connection device according to claim 10, wherein said adjusting means includes an adjusting ring, rotatably provided on the outer periphery of the lens barrel, for moving the lens system in accordance with the rotation movement and in the axial direction of the lens barrel.

* * * * *

UNITED STATES PATENT AND TRADEMARK OFFICE
CERTIFICATE OF CORRECTION

PATENT NO. : 4,697,894

DATED : October 6, 1987

INVENTOR(S) : Takamura et al

It is certified that error appears in the above-identified patent and that said Letters Patent are hereby corrected as shown below:

Title page, Item [30] should read:

[30] Foreign Application Priority Data

Nov. 30, 1984 [JP] Japan...........59-253078
Nov. 30, 1984 [JP] Japan...........59-182018[U]

Signed and Sealed this

Thirty-first Day of May, 1988

Attest:

DONALD J. QUIGG

Attesting Officer

Commissioner of Patents and Trademarks